(12) United States Patent
Lippe et al.

(10) Patent No.: US 6,171,276 B1
(45) Date of Patent: Jan. 9, 2001

(54) AUTOMATED DELIVERY DEVICE AND METHOD FOR ITS OPERATION

(75) Inventors: Barbara Lippe, Los Angeles, CA (US); Anders Holte, Täby (SE); Hans Himbert, Bromma (SE); Birger Hjertman, Vällingby (SE); Bohdan Pavlu, Nacka (SE); Magnus Westermark, Sollentuna (SE); Rainer Bosse, Kirchberg; Markus Adam, Signau, both of (CH)

(73) Assignee: Pharmacia & Upjohn AB, Stockholm (SE)

( * ) Notice: Under 35 U.S.C. 154(b), the term of this patent shall be extended for 0 days.

(21) Appl. No.: 09/129,357

(22) Filed: Aug. 5, 1998

Related U.S. Application Data
(60) Provisional application No. 60/058,177, filed on Sep. 8, 1997.

(30) Foreign Application Priority Data

Aug. 6, 1997 (SE) .................................................. 9702872

(51) Int. Cl.[7] .................................................. A61M 31/00
(52) U.S. Cl. .......................... 604/67; 604/65; 128/DIG. 1
(58) Field of Search ................................... 604/131, 154, 604/187, 218, 65, 67, 151, 207, 192, 194, 195–197; 128/DIG. 1, DIG. 12, DIG. 13

(56) References Cited

U.S. PATENT DOCUMENTS

| | | |
|---|---|---|
| 4,529,401 | 7/1985 | Leslie et al. . |
| 4,564,360 | 1/1986 | Young et al. . |
| 4,585,439 | 4/1986 | Michel . |
| 4,624,658 * | 11/1986 | Mardorf et al. .................... 604/121 |
| 4,717,384 | 1/1988 | Waldeisen . |
| 4,950,246 | 8/1990 | Muller . |
| 4,968,299 | 11/1990 | Ahlstrand et al. . |
| 4,978,335 | 12/1990 | Arthur, III . |
| 5,273,544 | 12/1993 | van der Wal . |

(List continued on next page.)

FOREIGN PATENT DOCUMENTS

| | | |
|---|---|---|
| 22763 | 7/1984 | (AU) . |
| 2710433 | 9/1977 | (DE) . |
| 4420232 | 12/1995 | (DE) . |
| WO8809187 | 12/1988 | (WO) . |
| WO9312726 | 7/1993 | (WO) . |
| WO9424263 | 10/1994 | (WO) . |
| WO9714459 | 4/1997 | (WO) . |

OTHER PUBLICATIONS

International–type Search Report for Swedish application 9702872–4 filed Aug. 6, 1997.

* cited by examiner

*Primary Examiner*—Sharon Kennedy
*Assistant Examiner*—Deborah Blyveis
(74) *Attorney, Agent, or Firm*—Dinsmore & Shohl LLP

(57) ABSTRACT

A delivery device including a) a housing, b) a container for a fluid arranged in the housing, the container having an opening, c) a delivery conduit connected in fluid communication with the opening, the conduit having a front end in flow respect distal from the container and a rear end in flow respect proximal to the container, the front end and the rear end defining an axis therebetween and a forward direction and a rearward direction, and d) a pump arranged to deliver fluid at least in a direction from the container through the conduit, the device comprising, a sensor able to change state in at least one respect in response to a predetermined proximity of an object to the sensor in a sensing direction, a converter, separate from or integral with the sensor, converting at least one of the sensor states into an electromagnetic signal, and a processor, receiving the electromagnetic signal and delivering a control signal to an operational component of the device.

36 Claims, 3 Drawing Sheets

U.S. PATENT DOCUMENTS

| | | |
|---|---|---|
| 5,360,410 | 11/1994 | Wacks . |
| 5,383,851 | 1/1995 | McKinnon, Jr. et al. . |
| 5,399,163 | 3/1995 | Peterson et al. . |
| 5,480,381 | 1/1996 | Weston . |
| 5,501,673 | 3/1996 | Hjertman et al. . |
| 5,520,639 | 5/1996 | Peterson et al. . |
| 5,535,746 | 7/1996 | Hoover et al. . |
| 5,536,249 | 7/1996 | Castellano et al. . |
| 5,549,560 | 8/1996 | Van de Wijdeven . |
| 5,593,390 | 1/1997 | Castellano et al. . |
| 5,611,784 * | 3/1997 | Barresi et al. .................... 604/211 |
| 5,716,338 | 2/1998 | Hjertman et al. . |
| 5,868,710 * | 2/1999 | Battiato et al. .................... 604/123 |
| 5,989,221 * | 11/1999 | Hjertman ............................ 604/131 |

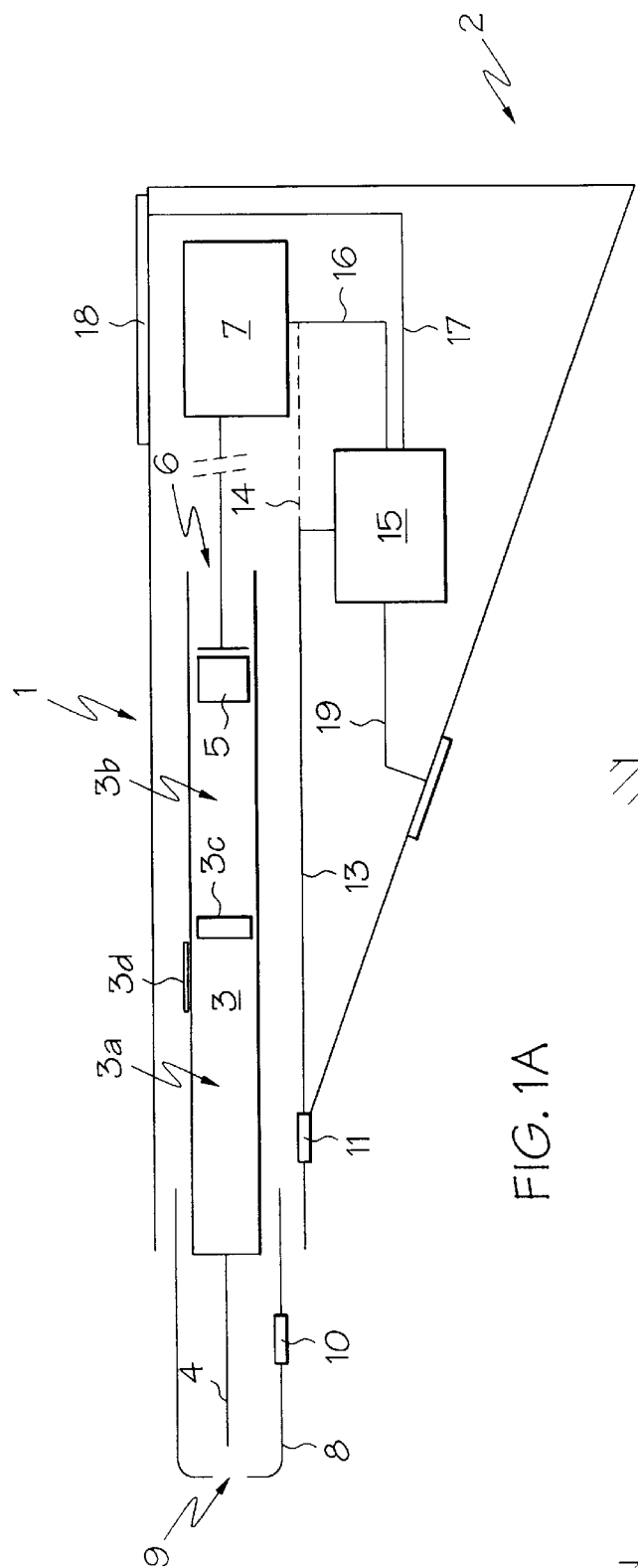
FIG. 1A
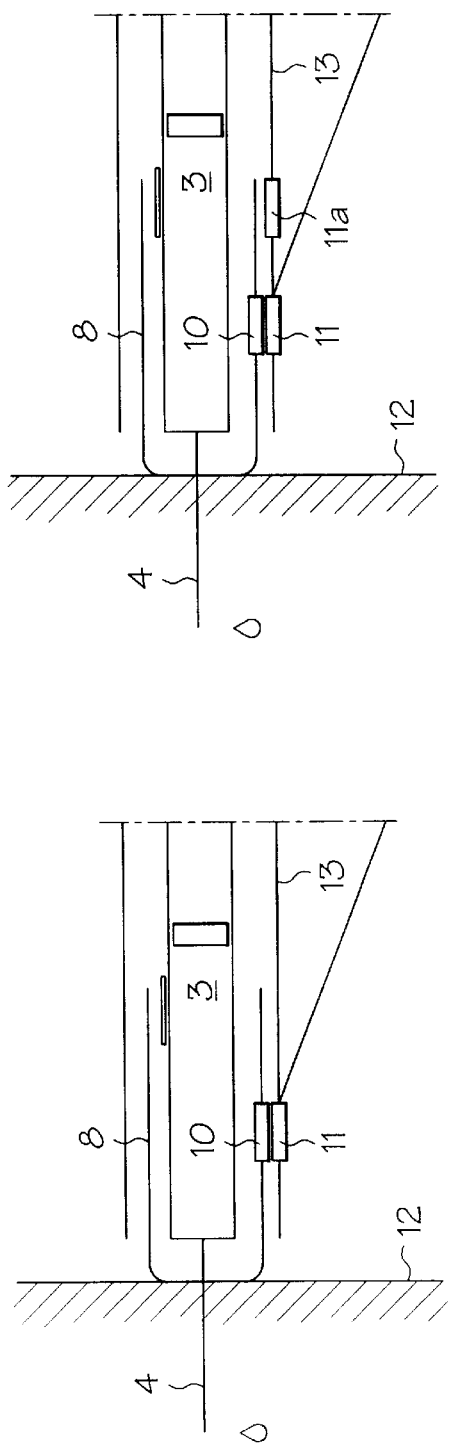
FIG. 1B
FIG. 1C

AUTOMATED DELIVERY DEVICE AND METHOD FOR ITS OPERATION

This application claims be benefit of U.S. Provisional Application No. 60/058,177, filed Sep. 8, 1997.

TECHNICAL FIELD

The present invention relates to a delivery device including a) a housing, b) a container for a fluid arranged in the housing, the container having an opening, c) a delivery conduit connected in fluid communication with the opening, the conduit having a front end in flow respect distal from the container and a rear end in flow respect proximal to the container, the front end and the rear end defining an axis therebetween and a forward direction and a rearward direction, and d) a pump arranged to deliver fluid at least in a direction from the container through the conduit. The invention also relates to a method for operation such a device.

BACKGROUND

Although delivery devices are known for use in a vast variety of applications the present invention is mainly concerned with injection devices in applications where the injection receiving object is solid or semi-solid and wherein the orientation of the injection device relative the injection receiving object is critical to the proper outcome of the injection. Typical applications are the administration of pharmaceutical preparations to humans or animals where orientation is important for diverse reasons. Depending on the nature of the preparation and the intention of the treatment the target tissue is vital for correct biochemical activity, availability and absorbency period. The intended injection site may for example be subcutaneous, intramuscular or intravenous. The dose delivered is often critical and erroneous treatment may result both from lost preparation due to e.g. inadvertent needle release or partial placement in wrong tissue. Conversely, especially larger volumes may intentionally be distributed at several depth during needle penetration or partially in slow releasing tissue and partially in fast releasing tissue.

These demands can be met also when using the simplest injection devices, such as the common hypodermic syringe, when in the hands of a skilled operator who also may initiate medically relevant corrective measures in case of accidents and malfunction. More or less automated devices has since long existed to enable laymen with limited training performing injections with reasonable safety in critical or emergency situations. Often the devices are designed for single shots only. A general trend in long-term medication is to place the administration responsibility on the patient himself, also in the case of child or disabled persons. Here the demands are still higher. The continuous medication requires the patient to cope with repeated dosing, perhaps with varying dose setting and proper replacement of emptied cartridges with fresh ones as in pen-type injectors. A high degree of automation and control is desirable to avoid mistakes, not only at the mere injections steps but also the critical initiation and preparation steps. Patients dependent on daily administrations also have a legitimate need for convenience and devices discrete enough to be brought around in daily life.

Mechanical automation is provided in common autoinjectors. Typically the user is expected to position the device in proper injection orientation against the skin and operate a trigger button. Stored mechanical energy, e.g. in a spring system, may then perform autopenetration into the tissue, autoinjection of the medical and possibly also automatic needle retraction. Simpler systems may not provide autopenetration but assume the user to make the needle insertion. Hence the devices give the operator little assistance in orienting and localizing the devices in respect to the body. Autoinjectors are also known that require the operator to press the device against the injection site in order to trigger the injector. Typical examples are disclosed in AU 563.551, U.S. Pat. No. 4,717,384, EP 518.416 and WO 93/23110. The help provided by such constructions is limited and inflexible and cannot be adapted for different foreseeable operational or hazardous situations. Pressure rather than position based triggering makes desirable adaptations still more difficult. Generally, once triggering has occurred, either intentionally or inadvertently, the operation sequence proceeds irreversibly. Moreover, the dislocation risks are generally high in mechanical devices due to rebound effects and the forced transitions involved.

Automated devices based on electronic or electromechanical principles have also been proposed. Disregarding here infusion pumps and similar injection devices for primarily hospital or permanent use, where device orientation generally is not critical, several prior patent specifications, as represented by e.g. EP 143.895, EP 293.958, DE 2.710.433, WO 93/02720, WO 95/24233 and WO 97/14459 as well as our copending applications SE 9602610-9 (U.S. 60/021,397) and SE 9602611-7 (U.S. 60/021,293), relates to hand held devices for direct action against the body. The known devices take advantage of automation principles in several respects, such as the precise and reproducible injection possible with electric motors, motor assisted autopenetration and mixing or reconstitution, cartridge identification, sample analysis, injection data collection and manipulation, dose setting, injector orientation relative gravity for proper mixing or deaeration etc. In spite of this diversity the automated devices in this class do not deal with device orientation versus the injection receiving body and do not solve any problem relating thereto.

Accordingly there is a continuing need for injection devices assisting the user in device orientation related handling steps and preventing or ameliorate consequences of mistakes and misuse resulting therefrom, especially useful for patients under self-administration. Although the present invention has a more general utility, it will mainly be described against this background.

SUMMARY OF INVENTION

A main object of the present invention is to avoid the disadvantages and shortcoming of known injection devices as described. A more specific object is to provide an injector assisting the user in proper orientation of the device in relation to the injection site. Another object is to provide a device being flexible and adaptable to different handling and operation situations. Still another object is to prevent or ameliorate consequences of unintended actions or misuse. Another object is to facilitate administration of the preparation in the correct target tissue. Yet another object is to avoid irreversible injection procedures. A further object is to avoid dependence on purely mechanical orientation means. Still another object is to offer orientation assisting means fully compatible with electronic or electromechanical automation means. Yet another object is to provide such devices with high simplicity in handling and suitable for patient self-administration or otherwise requiring limited skill and training.

These objects are reached with a device and method having the characteristics set forth in the appended claims.

By providing an injection device with a proximity sensor and a converter to derive an electromagnetic signal from the sensor several of the abovesaid objects are reached. The signal is immediately available for and compatible with any other electronic or electromechanical automation means present on the injector and reliance on purely mechanical orientation means is avoided. The signal can be recovered without requirements for pressure or high forces. Use of the transformed sensor output is highly flexible and can be adapted to a multitude of operation situations. If used in the device triggering sequence, inadvertent initiation can be avoided by requiring a predetermined characteristic to be present, such as a sustained or repeated signal, or making the signal operable only within a narrow sequence window. Similarly, irreversible operation procedures can be avoided by using the sensor output also for device disabling purposes, for example to stop an injection if the device is moved to an improper position. For similar reasons the device can be made selective in respect of target tissue by allowing injection only at predetermined penetration depths. Manipulation mistakes can be prevented if the signal is used to warn or alert the user before given displacement tolerances have been passed. The total handling relieves available serve to make the device excellently suited for applications where simplicity is vital, as in many cases of patient self-treatment. The principles used are compatible with most manual or automatic injection initiation, operation and termination steps and may for example be adapted to automatic penetration, injection and needle retraction, when present. The device itself need not be more complex than necessitated by other considerations, especially not when using existing parts, such as a needle cover, also for the sensing purposes.

Further objects and advantages with the invention will be evident from the detailed description hereinbelow.

DETAILED DESCRIPTION

As indicated in the introduction the injector described herein may be used for a variety of purposes within and beyond the medical area and for any type of preparations, such as chemicals, compositions or mixtures, in any container and delivered for any purpose. For reasons outlined the system has certain special values in connection with medical delivery devices where also the design constraints are more severe than in most other applications. For convenience the invention will be described in terms of this application.

The principles of the present invention may be used for delivery devices or systems in broad terms. The delivery conduit from the device may be an infusion channel or any conducting means such as a tube or catheter, a needle or cannula or a needle-less system based on liquid jet or a particle gun with gas propellant. The container content material shall be deliverable by use of a delivery mechanism, also referred to herein as a pump, and any material fulfilling this requirement can be used. Normally the material is a fluid and preferably a liquid, including materials behaving as liquids such as emulsions or suspensions. These observations relates to the final preparation whereas other components, notably solids, may be present before final preparation. The nature of container content shall also be understood to include medical in broad terms and to embrace for example natural components and body fluids prefilled or drawn into the container although most commonly the medical is factory prepared. The invention may assist in solving special problems in connection with sensitive compounds susceptible to degradation or denaturation under mechanical stress such as high shear forces. Compounds of high molecular weight may be of this type, high molecular weight hormones for example growth hormones or prostaglandins. The invention may also assist in solving special problems in connection with medical requiring a preparation step immediately prior to the infusion, typically a mixing of two or more components, which all may be fluid or may include a solid as when dissolving a lyophilized powder in a solvent, such as hormones or prostaglandins.

The administration manner can also be varied within broad limits and may include entirely continuous infusion, continuous infusion with varying flow or intermittent infusions or injections with repeated either equal or varying doses. Especially when combined with automation means in a preferred way the administration manner can easily be varied by adaptations in software or similar control. In portable devices the intermittent administration is common. Similarly, although delivery devices may be contemplated also for a single dosing operation, generally they are designed for more than one or multiple individual doses for intermittent administration.

In addition to the basic functions for delivery purposes the delivery system with preference may include other valuable features such as for initiating the container and its content and provide various checks and controls of both the container and the pump part electronics and mechanics.

The invention may be applied to delivery devices in stationary or permanent set-ups. For reasons to be explained the invention give special advantages in delivery devices for ambulatory purposes, especially those being autonomous with on-board energy storage, motor and processor means and in particular small hand-held devices of truly portable nature.

As said in the introduction a preferred delivery device can be said to generally comprise at least a) a housing, b) a container, c) a delivery conduit connected in fluid communication with the container and d) a pump arranged to deliver fluid at least from the container through the conduit.

The Housing

The device housing shall be understood in general terms and mainly represents the point of reference, unless otherwise indicated, for movements and also the point of reference for forces applied by actuating means performing said movements, whereat the force is applied between the housing and the moving or gripped part. Movable parts may be present in the pump arrangements or e.g. in parts performing mixing, autopenetration, needle ejection and retraction etc. The minimum functional requirement is that the housing offers a support or platform for the movable parts and the actuating means providing the movements and forces. As in common practice, however, it is preferred that the housing forms a container at least partly embracing the parts and preferably also to such an extent that only the features designed to be controlled or monitored by the operator are externally exposed.

The Container

The container part shall be understood in broad sense and may take a variety of forms such as any kind of tube, vessel, flexible bag, vial, ampoule, cartridge, carpoule, syringe body etc. There are some advantages in using containers that are rigid, at least at its opening or the part for attachment to the mechanism but preferably generally rigid, such as vials, ampoules or syringe bodies. Common container materials such as glass or plastic can with preference be used. The container may be an integral or composite structure, such as including an outer casing or any other multipart construction for closures, fixtures, protection etc., and whenever used herein "container" shall be understood to include any auxiliary part present. The container may be integral with the housing, e.g. for use in disposable injectors, when the container is refillable or when the container is part of the pumping system repeatedly drawing the preparation to be injected from an external source or channel before each injection stroke. The container may also be separate, e.g. for allowing replacement in case of disposable prefilled containers, for simple sterilization or scrapping in case of change of content type or patient. As known per se more than one container may be present, e.g. in case it is desirable to perform a mixing before injection, mixing during injection when drawing a part volume from each container or in case of sequential injection of different components.

The container has at least one opening through which the medication pass during the main delivery operation of the device, either from the container interior to the surrounding for e.g. administration of the medical to the patient or to the container in case of aspiration of body fluids or at preparation steps such as filling, mixing or dissolution in the container, during which operations the opening need to be present. It is possible and even in many situations preferred that certain device operations, such as initiation, takes place before communication has been established and the opening requirement shall then be considered satisfied by the preparation means for creating the communication such as the presence of a removable closure or a pierceable or rupturable part on the container itself as in the case of an ampoule or bag or a specially designed part as in case of penetrable membranes or septum. All communication may take place through one opening, for example both medical passage and pressure equalization in a rigid container or by delivery from a container which is flexible or has a movable or deformable part but nothing prevents that further openings are provided for similar purposes, which can be identical to the at least one opening but which can be entirely different and for example be adapted for another purpose of e.g. infusion or syringe type with a movable wall or piston.

The container may be a simple bottle, vial or bag in case the delivery device is arranged to withdraw, continuously or intermittently, metered amounts therefrom for delivery as defined. Often, and especially in connection with self-administration, the container type is more elaborate and is commonly in the form of a cartridge, being the container part of a syringe type of delivery system, which may be still more elaborate in the case of multichamber cartridges. A cartridge for the present purposes may generally be said to include a vessel having a front part and a rear part defining a general cartridge axis, an outlet for the preparation arranged at the front part and at least one movable wall arranged at the rear part, a displacement of which wall causes the preparation to be moved towards or expelled through the outlet. Vessel shape and movable wall have to be mutually adapted. The vessel may have a substantially constant internal cross-section, with a similarly constant vessel axis, between front and rear parts giving a generally tube-shaped vessel, and most preferably the cross-section is of the common circular type giving a substantially cylindrical vessel. The movable wall is then preferably a substantially shape-permanent, although possibly elastic, body sealingly adapted to the internal vessel surface and preferably of the piston type.

Dual or multi chamber cartridge types are known e.g. for preparations demanding a mixing of two or more components or precursors before administration. The components are kept separated by one or more intermediate walls of different known designs, which walls divide the vessel into several chambers, sometimes placed parallel along cartridge axis but most commonly in stacked relationship along the axis. Unification of the components may take place by breaking, penetrating or opening a valve construction in the intermediate walls, for example by introducing a pin or needle through the cartridge front, through or at the rear movable wall or by means at the cartridge exterior (compare e.g. the cited WO 93/02720). In another known design the intermediate wall or walls are of the plunger type and flow communication between the chambers is accomplished by moving the plunger to a by-pass section where the interior wall has one or several enlarged sections or repeated circumferential grooves and lands in a manner allowing by-flow of rear chamber content into front chamber at displacement of the rear movable wall (compare e.g. U.S. Pat. No. 4,968,299 or WO 93/20868 and WO 95/11051). The chambers may contain gas, liquid or solids. Generally at least one liquid is present. Most commonly in pharmaceutical applications only two chambers are present and typically contains one liquid and one solid, the latter being dissolved and reconstituted during the mixing operation.

The Conduit

In general terms the delivery conduit is connected in fluid communication with the opening of the container and has a front end in flow respect distal from the container and a rear end in flow respect proximal to the container. In its most basic form the conduit can be seen as a continuation of the container opening. In this sense the front end may be of any nature including an connection to another conduit, e.g. any of the common infusion channels mentioned. It is preferred, however, that the front end is the termination of an injection channel adapted for delivery of the preparation to the target site, e.g. on or in the patient, for which purpose at least the last, frontmost, part of the conduit should be suitable for delivery to the site. Depending on the delivery mechanism used the front end may not be designed for direct contact with the target site, as in case of liquid jets, powder guns or sprays, where the front end may be an orifice or nozzle for positioning at a distance from the target or on the surface of the target in spite of that the true target is below the surface. In other instances the front end is designed for penetrating into the target as in case of cannulas or common needles. The channel between the front end and the rear end may be curved or bent, as for a flexible infusion tube or in an on-board permanent connection, although in many applications it is desirable that the conduit is substantially straight, as for a needle on a syringe. Generally at least the last, frontmost, part of the conduit defines in flow sense an exit axis and a forward direction and a rearward direction. Positional and directional statements will be given in relation hereto unless otherwise indicated.

The Pump Mechanism

The mechanism for delivery of medical through the container opening should basically include at least one type of pump which may have to be selected for the special kind or container and medical used. The pump may include any kind of pressure source, such as mechanical or electrolytic pressure build-up, in the container and suitable valve means for control, which method can be used with virtually any kind of container and any kind of product, such as transdermal delivery of powder, as exemplified by WO 94/24263, similar delivery through liquid jets, as exemplified by WO 94/2188, or regular tube infusion, as exemplified by WO 88/09187. Any kind of container can also be used with pumps based on peristaltic action or centrifugal action, although also for general use pumps based on controlled positive displacement are preferred and especially such pumps based on a separate cylinder and piston action, as exemplified by U.S. Pat. No. 5,480,381 for liquid jet or U.S. Pat. No. 4,564,360 for a manually operated needle based device. The common syringe type container need a specialized pump system. Either the mechanism is adapted to act on complete syringes, having their own piston rods, by engaging and axially displacing said rod, as exemplified by the initially referenced U.S. Pat. No. 4,978,335, which may be preferred when it is desired to accommodate syringes of many different types and sizes, or the mechanism has a piston rod acting more or less directly on the piston of a cartridge type container, as exemplified by WO 95/26211, EP 143.895 or EP 293.958, which can be made smaller and more adapted to portable devices. Also dual or multiple chamber cartridges can use a similar devices for its various phases, as exemplified by the initially mentioned WO 93/02720. Although the various pump mechanisms discussed may include mechanical means for affecting the medical or a piston the means, such as a piston rod, may be actuated by any known means, such as gas pressure, vacuum, hydraulics, springs or manual operation. It is preferred to actuate the pump mechanism by electric devices such as an electrical motor, indirectly or preferably directly, among others because of its ease of adaptation to an overall automated device.

The mechanism may preferably include further components. The mechanism may for example include special means for securing doses delivered, e.g. by direct metering of medical delivered, although it is generally preferred to utilize directly or indirectly the pump for this, e.g. by monitoring axial displacement or the rotation of a piston rod axis in a manner known per se. In particular it is preferred that the mechanism includes a control system operative to perform at least part of the abovementioned administrative patterns, initiation of containers or cartridges, self-control or surveillance and possible recording of operation steps conducted. Such systems are known in the art, as exemplified by U.S. Pat. No. 4,529,401, and may be designed in a multitude of ways. For the purposes of the present invention it is preferred that the control system drives and monitors at least part of the sensor system and processes data obtained therefrom.

The Proximity Sensor General

The principles of the present invention may be utilized in connection with any injector whenever it is desirable to establish distance or orientation between any of its part and an object. The object may be the operator, e.g. to disable the device unless presence of an operator is positively verified. The object may be communication link part, e.g. in order to secure proper transmission in case of data exchange.

In accordance with a main purpose, of securing a proper position, the object is the injection target, e.g. the patient or animal to receive the delivered or injected preparation. In order to accomplish this feat it is preferred that the sensor is positioned so that its position relative the conduit front end is given. In case the conduit front end is not given in relation the housing, as when using a flexible tube conduit, this may require that the sensor is arranged fixed in relation to the front end to assist the user in localizing this end. This arrangement may also require a wire or other communication link to the housing in case the signal is to be used or processed by automation means in the housing. There are advantages in using the invention in connection with injection devices with given spatial relationship between conduit front end and the housing. The conduit may still be movable in relation to the housing, e.g. with needle exposure and retraction as is common in autoinjectors or simply for accessing the needle or its cover or adjusting penetration depth, but is then normally guided in a predetermined and fore-seeable way. In these cases of conduit front end arrangement on the housing the sensor can be arranged at said conduit front end. Preferably the sensor is fixed in relation to the housing. The invention has with success been utilized in connection with needle based injectors where location is critical for reasons discussed in the introduction. The sensor positions given here shall not exclude that the sensor itself comprises movable parts as in the case of a switch.

Sensing direction in relation to the injection target depends on the purpose for the device positioning and the sensing direction can be entirely independent of delivery or injection direction, e.g. in the injection in the injection independent situations indicated above. Also when the desired device orientation is related to the injection direction the sensing direction may be different from the injection direction, e.g. normal or reverse thereto, for example if there is a reference surface other than the injection target surface as when working in a body cavity or relative a fixture. In less complicated situations it is preferred that the sensing direction has at least a component parallel to the injection direction, or to the conduit axis at the front end as defined. A sensing direction in an angle to the injection direction, especially an acute angle, may be used, e.g. to secure a proper starting position when inserting a needle laterally or sloping towards the target surface as is common when introducing a needle or cannula a certain safe distance although to a limited depth or when body access does not allow more perpendicular approach as in dental applications. In most applications it is preferred to make the sensing direction substantially parallel with the injection direction.

Sensor Type

Sensor type selection may be dictated by numerous circumstances such as the purpose of sensing, the object nature and target type, further signal processing, space consideration, energy available etc. Generally suitable sensing principles and components are known and can be used as such or with design adaptations for the present purposes.

It may be desirable to use contact-free sensors able to detect the presence of or proximity to an object also with the sensor at a distance from the object, e.g. to allow a free positioning with respect to other device parts and constraints, to maintain operation access in limited spaces, to prevent sensor contamination, to protect a fragile sensor from damages, to adapt sensing to an otherwise contact-free injector type of for example liquid jet or powder gun type etc. Sensor types for this purpose may be based on for example heat, IR, or radio sensing. Common components can be used such as, but not limited to, thermistors, thermoresistors, IR-receivers etc., which components as such, or the electronic circuits connected thereto, may be tuned for a certain target temperature, e.g. body surface temperature. When including a transmitter, e.g. radio, IR or ultrasound, a receiver can be set to give a signal at a certain distance based on amplitude, frequency, phase or shielding affected by the target. A preferred method being capacitive or inductive sensing, which is simple, reliable and adaptable to both target type and distance. The desired signal may be derived from a change in capacity or electromagnetic field when influenced by the target. All the methods mentioned are able to detect the presence of an object by change in the corresponding parameter and also to provide the desirable electromagnetic signal necessary by use of existing and commercial components. Nothing excludes that the device also incorporates parts to be in contact with the object, e.g. a sleeve or any other spacer structure for the purpose of assisting in stabilizing the device during injection, which structure in this case need not be arranged to provide the proximity signal. When desirable the abovementioned sensor types can also be used in direct contact with the object, either to obviate the need for the additional structures or to provide additional contact assistance.

Contact between injector and object is necessary when the preparation is to be introduced into the object through a channel such as a needle, cannula or infusion tube. As indicated in many situations it is desirable to have additional contact between injector and object, e.g. to stabilize the device during injection, to relieve the operator by resting the device on or even attaching the device to the object, to compress or stretch the skin of a patient at the injection site, to distract the patient from the penetration pain etc. Any of the above mentioned proximity sensors operational at a distance can be used also in contact with the object, with or without a protruding member as described. In case of contact, however, the sensor with preference can be made in the form of a contact sensor. The mechanical contact can be sensed for example as the pressure exerted between sensor and object when the parts have the desired predetermined relative positions, which method may also be adapted to respond only when a certain predetermined contact pressure is present, e.g. for proper injection or as a safeguard against recoil forces. The sensor may comprise a true pressure transducer, a piezoelectric device or a switch biased with for example mechanical means, such as a spring force or a yielding snap type lock. Pressure sensing need not involve large movements in any sensor component. Contact may alternatively be sensed as the displacement of a movable part caused by the object at relative movement therebetween. Displacement sensing can be made simple and require only low forces. The displacement in turn may be registered as such, e.g. as a current induced in a coil by the movement, which additionally may provide a speed signal. The displacement may also be registered as the location of the movable part when in the critical position, which can be done with any of the pressure detector as mentioned but a switch type detector may be sufficient. Any switch type can be used, for example based on optical detection, e.g. by a photoelectric element or IR transmitter and receiver, of the movable part in the critical position. Conventional mechanical switches can be used having movable contact surfaces, e.g. standard microswitches or application specific designs with contact means open or closed by the movable part. For reliability reasons it is preferred to use switch elements indirectly affected in the switching position, e.g. Hall elements or tongue elements affected by a magnet or relay elements affected by an induced current from a movement, and especially those being encapsulated. The displacement may be give a signal only in the desired end position, which is sufficient for many purposes, but may also provide signals along the path, either continuously or at multiple discrete locations, e.g. to monitor proper use of the device or when providing adjustable proximity sensing. The displacement of the movable part is typically larger than in pressure sensing, say at least 1 mm, preferably at least 2 mm and most preferably at least 4 mm.

Independent of sensor type used the sensor may be provided on the delivery device as an additional component over those required for other purposes. It is preferred, however, to adapt structures for other purposes an additional sensing capability, which is most easily done with contact sensors. It is often preferred to arrange the sensor with a part associated with the device conduit. In case of contact free delivery, as in liquid jets, powder guns, sprays, inhalators etc., such devices often comprise a guiding or orienting part for contact with the object, such as a sleeve or orifice type opening for more general use or a part adapted to the specific target organ, such as mouthpiece, an eyecup etc., and it may desirable to associate the sensor with such parts. Similar parts may be present and utilized also when using delivery devices having conduits for contact with the object but here with preference the sensor may be associated with these conduit component, e.g. incorporating tubes, needles or cannulas. Often a movable cover is used over a tipped conduit for insertion into an object, which cover is pushed rearwards in connection with conduit insertion. The cover may be present to protect the conduit against damage or contamination, to protect the user from inadvertent pricking or to hide for example a needle from a patient to reduce anxiety. The sensor can with advantage be associated with such a cover so that the sensor in some way gives a signal in response to movement of the cover and preferably so that a distinguishable signal is received at proper penetration of the conduit. This principle can be used in connection with a flexible infusion tube if a cover is present, which is not always the case as infusion tubes are often inserted by skilled practitioners without need for assisting devices. Rather the advantages are most pronounced when the housing is gripped and used for conduit penetration, which is commonly the case at patient self-administration and which normally requires that the conduit is arranged fixed in relation to the housing in at least all directions but axial, where a mobility may be retained for e.g. autopenetration or needle protector removal, but in many instances the conduit is fixed also in the axial direction. The invention has been utilized with advantage with a sensor associated with a movable needle cover for an injector.

In all sensor arrangements described the sensor should be positioned so that a detectable signal change is obtained when the critical device part, forming a reference point, has the desired location in relation to the target object. In cases of non-contact between conduit and object this may be a distance suitable for delivery of the preparation, either a concentrated delivery for penetration as for a liquid jet or a distributed delivery as for a spray. The sensor may be a pressure sensor for a part placed against the object in the suitable position or a displacement sensor on for example a cover uncovering an orifice or a simple front switch. For penetrating conduits the sensor may be a pressure sensor placed so as to be engaged by the object at the predetermined penetration depth e.g. at the base of a needle or cannula, or a displacement sensor for a cover as described with a signal change at a predetermined displacement of the cover e.g. by a switch at the desired point.

As earlier indicated a sensor measuring direction may be in any desired angle although normally in the forward direction with respect to the conduit. A single sensor direction may be sufficient in most application although use of more sensors can be used to fix the position in other dimensions, e.g. two sensors to determine orientation in a given plane or three sensor to determine orientation in all three dimensions, for example when operating the device in a cavity.

Signal Use

The signal received from the sensor shall be in the form of, or transformed into, an electromagnetic signal representative for the proximity data as described. The electromagnetic signal may be based on electromagnetic radiation, such as an optical signal, but is preferably an electric signal. Many suitable components for use as sensors are designed to give such a signal output but may otherwise be inserted in a circuit securing such an output. Any inherent, integral or separate arrangements of this kind can be regarded as a converter for sensor output into the electromagnetic signal. The electromagnetic signal so received or transformed is in general terms processed in a processor to deliver a control signal. The control signal in turn is used to control a functional or operational component of the device. The operational components can be of any kind although some typical examples will be given below. The control signal can be of any nature, such as mechanical, optical etc., depending on its further use but is preferably an electric signal.

The control signal may be used to issue a message to the user, e.g. to warn or alert the user of an improper position before the device is activated for delivery. The message may be a sound, a tactically sensible signal such a vibration, a visual signal in the form of a warning lamp or a more complicated message on a display etc. or any combination of such messages.

It is preferred that the control signal is used to control the basic device functions over the actions taken by the operator. The control signal may be used to enable or disable the device respectively, dependent on the proper proximity condition. The enabling/disabling may take place by an electromechanical link, such as a relay device blocking a mechanical function e.g. a piston rod or pump mechanism. Better is to use this function in connection with devices having at least some automation means for driving the device, such as an electric motor, the operation of which may be determined by the control signal. Still better is if the device further includes processor means for control of the motor means, e.g. in order to secure proper cartridge control, initiation, sequencing of actions, dosing, feedback of administration data etc. in which case the electromagnetic signal can be fed to the processor for further flexibility, e.g. allowing the processor to issue a motor activation control signal only when the proximity condition is fulfilled or only when the abovesaid initiation steps have been properly concluded or proper condition has been positively verified in a self-control program. An existing processor unit may here act as the processor between the electromechanical signal and the control signal.

The control signal may further be used to actually trigger the device, i.e. as soon as the sensor signals the predetermined proximity condition an automatic function starts. As for the enabling/disabling condition just described this triggering function can be used for purely mechanical driving means via an electromagnetic release mechanism, better together with electric motor means an most preferably with processor controlled automation in the device.

The operations actually enabled or triggered can be of various nature. Preferably at least the injection is affected, in multidose devices perhaps including mechanical but preferably electric control of the dose delivered. In autoinjector type devices the autopenetration step may also be affected, preferably so that the sequence of autopenetration and autoinjection is controlled, possibly with a final needle retraction step. Autoinjectors are known which either deliver preparation also during the penetration phase or enable the injection first at completed penetration and the invention is compatible with both modes of operation. In case of multichamber cartridges with overflow or by-pass arrangements, which are known as such, the injection procedure may incorporate injection of different preparations in sequence, such as an anesthetic followed by an active ingredient or an active component followed by an rinsing component.

If the critical proximity value is made adjustable, either electronically in the processor e.g. by selecting different electromagnetic signals from discrete or continuous outputs or mechanically e.g. by making the sensor movable relative the housing, the use flexibility further increases. The device can be adapted to different conduit characteristics, e.g. needle lengths, couplings and construction and to different injection depth, e.g. type of tissue such as subcutaneous, intravenous, fat or muscle. The device may also be adaptable to local object target site conditions, such as necessary local penetration depth for the target tissue type, which can be made manually by a skilled operator or automatically if the device in a manner known per se is equipped with means for distinguishing different target types, e.g. based on penetration force or injection pressure feedback.

If is preferred that the sensor delivers different distinguishable electromagnetic signals for different proximity values, again either a continuous signal from a non-contact sensor or a contact sensor with a displaceable member giving continuous or multiple discrete electromagnetic signal along its path. Now more advanced administration patterns can be assisted by the sensor, for example delivery of preprogrammed amounts, or components in case of multichamber devices, at different depths or a continuous spread of a larger volume over a range of penetration depths.

The sensor electromagnetic signal may with preference be analyzed by the processor not only in respect of absolute distance value but also in respect of the change of said distance value over time in order to provide additional valuable information. If combined with a given penetration force or injection backpressure force the data may be indicative of the object nature, e.g. tissue type, or of misuse e.g. a stroke or hit rather than proper penetration or a way for guiding the user to such a predetermined suitable insertion speed.

All of the above applications of the sensor signal are facilitated by the presence of at lest some electromechanical means in the device to be further described hereinbelow.

Signal Processing

Generally for full utility the device should be combined with suitable electronics to drive the active elements of the sensor and to extract the electromagnetic signal therefrom. The processor electronics should at least be able to detect the sensor output, either for extraction of continuous or discrete data and put it to use via the control signal, e.g. in any of the manners exemplified, for which purposes the processor may at least adapt and/or transmit the electromagnetic signal to an operational component. Preferred signal processing will be exemplified below.

The electromagnetic signal from the sensor may be a simple single on/off signal, as received from a switch type sensor component, and can be sufficient for many purposes e.g. a plain triggering or enabling command. A quasi-continuous signal may be received from e.g. multiple on/off switches for example along a displacement path or levels of mechanical pressure resistance. A true continuous signal may be received from may sensors such as the noncontact types mentioned, from pressure transducers, piezoelectric devices or drossel and magnet based motion sensors. Examples for use of these responses have been given under preceding headings.

A simple on/off signal can be used as such a switch in e.g. simple motor enabling circuit or as an analogue but preferably digital input signal in a more sophisticated processing for automation or control. A quasi-continuous signal may be used similarly of each of the multiple switches has independent circuitry to enable distinction therebetween or as a continuous signal having a frequency of on/off pulses if the switches are arranged in parallel. A truly continuous signal contains still more information and can be treated in another way than the on/off signal.

Although all of the signal types may be used in a simple manner there are some advantages in using the signal in a more sophisticated manner. Firstly, more user information may be extracted from the signal. Secondly, signal information may be used to compensate for random factors in the device response to extract a more reliable treated signal. Thirdly, previous hardware feature may be replaced by software e.g. to permit a smaller or simpler device.

Accordingly the sensor output may be monitored for its signal, e.g. amplitude, versus a variable function, directly or indirectly, and the finction processed before an activity is based thereon. The variable may be distance, forming an signal versus distance function, e.g. when a movement as such is to be monitored, but the variable is preferably time, forming an signal versus time function. The finction obtained may be treated as continuous but it is preferred that values are sampled from the device output, which may be made at irregular but preferably at regular time intervals at a certain frequency. Sampling can be in any of several known ways. The sampling may be digital in the sense that the amplitude is compared with a reference level and either set to a binary 1 or a binary 0 depending on whether the amplitude is above or below the reference level, which may be varying but preferably is fixed. Among others for extracting more information from the raw data an analog sampling method is generally preferred, in which the finction absolute amplitude value is repeatedly registered. The analog value can be processed in an analog processor but it is mostly preferred to convert the value to digital form and process it in a digital processor. The signal may in a manner known per se be filtered to remove certain frequency ranges or noise.

The function values may be memorized and processed at any time and rate but real time processing is generally preferred in most applications, which may still require some memorizing of the values to be simultaneously processed at any given time. It is preferred that the processing involves at least two, preferably three and most preferably a multiple of function values at a time. Processing may take place in any known kind of analog or digital processor, preferably comprising a microprocessor such as a standard microprocessor or an application specific integrated circuit.

The processing may be operative to extract any kind of positional versus time information for recording or immediate action for any of the purposes exemplified. It is preferred, however, that the processing additionally serve to modify the raw signal from the device to make it more reliable for its intended purpose, some of which modifications will be exemplified.

The processing may perform an analogue to a physical dampening of the device or sensor movement. In continuous rest positions this may be achieved for example by filtering out certain frequencies, averaging out movements around an equilibrium point or extrapolating a regression curve. In discrete rest positions a similar result may be based on delayed or repeated check for amplitudes corresponding to a position corresponding to a stable rest position.

The processing may perform calibration of the device, for example by recording the actual device output at defined conditions, either staticly e.g. for discrete positions, or dynamically for continuous movements, and/or device response to various disturbances for example in respect of changes on driving conditions, ambient conditions etc.

The processing may perform an analogue to provision of physical hysteresis for device movements for example by requiring a certain degree of amplitude alteration for emitting a signal corresponding to a change from one position to another, e.g. to suppress frequent flipping around an equilibrium point.

Independent of which signal processing principle are applied there are some capabilities of special value in the present context. Contrary to mechanical solutions the signal processing should preferably provide some kind or reversibility in operation, i.e. after triggering an operation sequence, perhaps based on the sensor condition, the sequence should be possible to influence by a prescribed signal condition from the sensor. If for example the sensor signal indicates that the position is not any longer suitable for the current operation phase, such as penetration or injection, the device should be able to at least issue a control signal alerting and enabling the user to perform corrective measures, preferably also halt the operation phase in abidance of completed correction, and preferably also a recalculation or reprogramming of the processor means to deliver a complementary dose or additional dose, perhaps dependent on the coming time delay, at the following injection.

Convenient use of a reversibility capability would also benefit from the abovesaid hysteresis feature, i.e. the device should allow for some tolerances between enabling and disabling or operation and reversal. This feature can be provided by signal processing means as above exemplified but also by sensor design e.g. by giving a switch type sensor contact surfaces of the desired length or a bi-stable switch a mechanical bias having a certain inactive pressure range.

Preferably the device is also equipped with automation or processor means responsive to the sensor output only at a predetermined window in the operational sequence, e.g. after proper cartridge identification, mixing, deaeration, delay, dose setting etc. The means may also be responsive to a sensor output fulfilling certain characteristic criteria, e.g. speed of change, sustained stable change or repetition of change, to distinguish between proper condition and improper, inadvertent or accidental affirmance.

Hardware

The sensor system of the present invention may give advantages also in entirely manually operated delivery devices or in mechanically driven devices, such as with manually cocked spring systems, for example when the sensor signal is used for alarm, indication and signaling purposes. As has been indicated it is preferred that sensor signal is used in automated devices for which purpose the device should include actuating means comprising at least one electromechanical device with energy storing means, such as a battery, for driving purposes. The connection between the sensor and the electromechanical device can be of different kinds. The sensor signal can be a simple switch directly affecting the electromechanical device. In order to make the additional functions described possible a more complex connection may be needed, either a hard wired circuitry with discrete components or preferably a general processor means such as a general purpose microprocessor or an application specific integrated circuit.

The electromechanical device can be any device that can be affected by electrical means to give a mechanical force. The electromechanical device can be a relay or solenoid type device or preferably an electric motor. It is preferred that at least the pump mechanism is controlled or affected by the electromechanical means. With preference also other functions are controllable by electric means, penetration means with possible return means. For simplicity these additional capabilities may not need electromechanical driving means of their own but may be driven by mechanical means, such as springs, cocked manually or by simple electromechanical means. For highest flexibility, though, at least electromechanical release means e.g. solenoids, and possibly separate electrical motor means, should be present for such additional functions.

SUMMARY OF DRAWINGS

FIGS. 1A and 1B illustrate schematically a preferred device having a sensor in the form of a displaceable needle-cover, FIG. 1A and FIG. 1B showing the cover in extended and retracted position respectively.

FIG. 1C illustrates an alternative embodiment of the device wherein the converter is separate from the sensor.

DESCRIPTION OF DRAWINGS

Figure 2A:
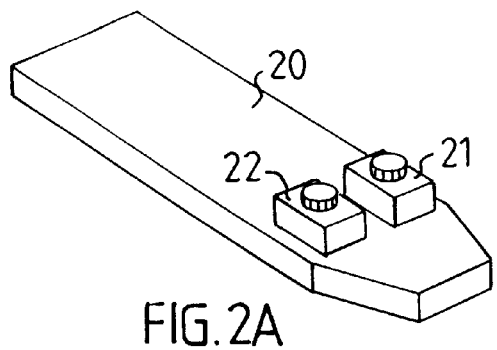
FIGS. 2A, 2B and 2C illustrate schematically a circuit board with switches cooperating with two different needle guards.

FIG. 1A and 1B illustrate schematically a preferred device having a sensor incorporating a displaceable needle-cover. The device is generally designated 1 and comprises a housing 2, a syringe type container 3, having a front end with an injection needle 4 and a rear opening with an inserted movable wall or piston 5. The container 3 may separate two or more components or precursors before administration.

For instance, the container 3 may separate the components by one or more intermediate walls of different known designs for dividing the vessel into several chambers. In one example, as shown in FIG. 1A, the container 3 may be divided into a front chamber 3a and a rear chamber 3b by an intermediate wall 3c. The intermediate wall 3c may be formed as a plunger type wall such that communication between the front chamber 3a and the rear chamber 3b is accomplished by moving the plunger type wall 3c to a by-pass section 3d where the interior wall of the container 3 has one or several enlarged sections or repeated circumferential grooves and lands in a manner allowing by-flow of the rear chamber content into the front chamber 3a at displacement of the rear movable wall or piston 5. The piston is affected by plunger 6 actuated by electric motor 7. Over the needle 4 is arranged a cover 8, coaxial with the needle and axially displaceable along the needle so that the needle can be exposed through hole 9 in the cover front. Attached to or integral with the cover is a structure 10 adapted to affect switch type element 11 on housing 2. In FIG. 1A cover 8 is in its frontmost position, shielding the entire needle 4 and with cover structure 10 disaligned with switch 11. In FIG. 1B the front part of device 1 is shown when brought into contact with an object 12, causing the cover to retract to a rear position in which the needle has penetrated into the object and structure 10 is aligned with switch 11. With preference the cover can be biased towards the frontmost position shown in FIG. 1A by for example a spring (not shown). Structure 10 can with preference be a small magnet fused into a cover of plastic material and switch 11 can be a component opening and closing in response to a magnetic field, such as a tongue switch element, giving an on/off signal in a circuit. It is clear that the arrangement described forms a proximity sensor in that a change of state is provided when the cover has been displaced by object 12 to the rear position in which switch 11 is affected by structure 10. Switch 11 is located fixed in relation to both the housing 2 and needle 4 hence the proximity sensed also bears a predetermined relationship to these parts, here with a given penetration depth for the needle. It is also clear that the change of state is inherently converted to an electromagnetic signal, here in the form of an on/off signal, which signal is transmitted via line 13. As shown in FIGS. 1A and 1B, for example, the switch 11 contains a sensor that is integral with a converter. Alternatively, as shown in FIG. 1C, the converter 11a may be formed separately from the sensor or switch 11. The signal may be used as such, as indicated by dotted line 14, e.g. to directly activate motor 7, but it is preferred to process the signal in a more elaborate way, indicated by the solid line leading to special processor 15. The processor 15 may be any of those exemplified earlier in the specification performing any of the tasks exemplified. It is preferred that the device is at least partially automated, e.g. with container control routines, container initiation routines, dose setting and monitoring routines, self control routines and message issuing routines etc., and that the same processor is used for at least some of such routines and for the present purposes, such as simply a check for a sustained signal in order to prevent inadvertent triggering and/or positive verification of any of the automatic functions mentioned. Illustrated is a first outgoing control signal 16, activating motor 7, and a second control signal 17, controlling the message on a display 18. The processor 15 may be arranged to directly trigger the control signals upon reception of a proper electromagnetic signal 13, or preferably also await for a manual control button operation signal 19 to thereby treat the proper electromagnetic signal 13 only as an enabling signal before manual triggering takes place. In both instances it is preferred that processor 15 continues to monitor line 13 to detect any significant deviation in position to thereby issue a change in control signals, e.g. issue a warning message over line 17 and perhaps an interruption in activation signal 16 for the motor.

Figure 2B:
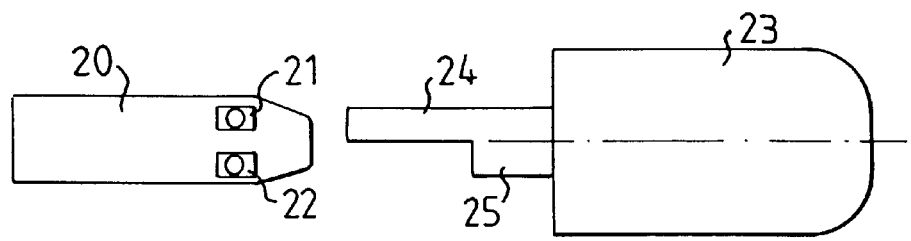
Figure 2C:
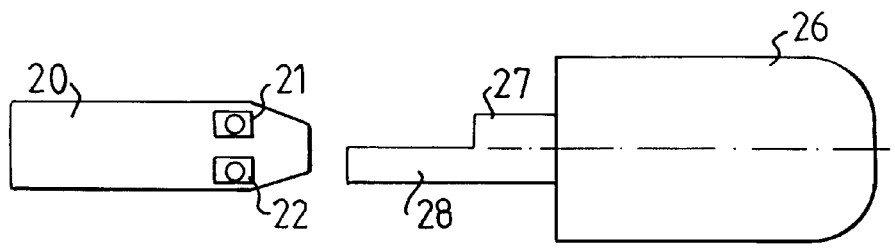

FIGS. 2A, 2B and 2C illustrates schematically a circuit board with switches cooperating with two different needle guards. Circuit board 20 is intended to be used in a delivery device of the general type described in FIG. 1 and may comprise (not shown) circuitry and components for any purpose described herein. Of current interest is that the board has first and second switches 21 and 22, forming parts of a sensor system together with two different needle covers 23 and 26 illustrated in FIGS. 2B and 2C respectively. Needle cover 23 as shown in FIG. 2B has an upper longer arm 24 for cooperation with first switch 21 and a lower shorter arm 25 for cooperation with second switch 22. When needle cover 23 is properly assembled on the delivery device the longer arm 24 is arranged to permanently close first switch 21, independent of the forward and rearward movements of the cover, thereby enabling the electronics to verify presence and proper installation of the cover as well as type of cover installed. Short arm 25 is arranged to close second switch 22 only when the needle cover has been moved to a rearward position whereas the switch is unaffected when the needle cover is in a forward position. It is clear that in the situation of FIG. 2B first switch 21 acts as a control while second switch 22 acts as a part of the sensing system. Needle cover 26 as shown in FIG. 2C is similar to that of FIG. 2B, save that here the upper arm 27, for cooperation with first switch 21, is the short arm and the lower arm 28, for cooperation with second switch 22 is the longer arm. It is clear that in the situation of FIG. 2C second switch 22 acts as a control while first switch 21 acts as a part of the sensing system. It is also clear that the arrangement described in FIG. 2 is able to distinguish between which type of needle cover, 23 or 26, has been installed to make possible different device behavior depending on which needle cover is used. A preferred use of this capability is to make the device automatically delivering fluid when the needle cover has been moved to the rear position without need for further actions, when one of needle cover types 23 and 26 respectively is installed, whereas when the other needle cover type is installed the device is only enabled when the needle cover is moved to the rear position so that a further action is needed to actually trigger the delivery, preferably the activation of a manual button. Although needle covers 23 and 26 have been described as different parts it is equally possible to equip a single needle cover with two different sets of arms which selectably can be aligned with the switches, e.g. by arranging the arm structures of FIG. 2B and 2C respectively on diametrically opposed sides of a single needle cover and making transformations therebetween by 180 degree turns of the needle cover.

Figure 3A:
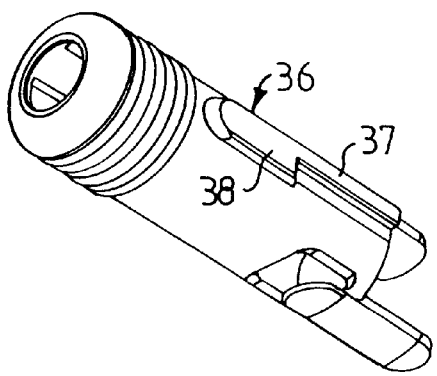
FIGS. 3A and 3B show in two views a preferred design for a needle cover utilizing the principles described in connection with FIG. 2.
Figure 3B:
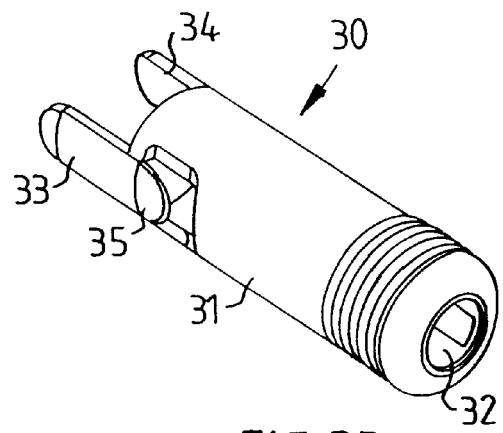

FIGS. 3A and 3B show in two views a preferred design for a needle cover utilizing the principles described in connection with FIG. 2. As best seen in FIG. 3B the needle cover 30 comprises a body 31 having a front hole 32 for exposure of a needle when the needle cover is moved rearwards. In the rear end legs 33 and 34 are arranged for attachment of the needle cover to elongated slits (not shown) on the delivery device, which attachment is facilitated by the resilient nature of the legs and locking flip 35. Guided by the slits the needle cover 30 can move between a forward and a rearward position. As best seen in FIG. 3A a contact structure 36 is arranged on the body 31 of needle cover 30. Contact structure 36 provides a long arm 37 and a short arm 38. Arms 37 and 38 has the same function as the arms described in connection with FIG. 2, i.e. the long arm 37 permanently depressing one switch on the device and the short arm 38 depressing another switch on the device only when the needle cover 30 has been brought to a rear position in which a suitable length of the needle is exposed through the hole 32 outside the needle cover.

Figure 4A:
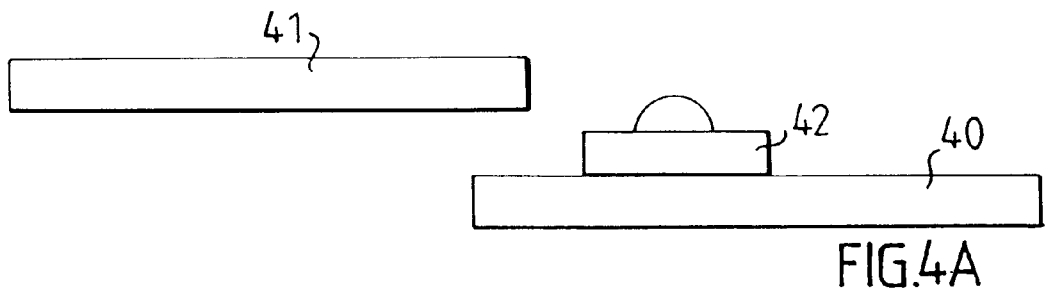
FIGS. 4A to 4D schematically illustrate alternative switch elements.
Figure 4B:
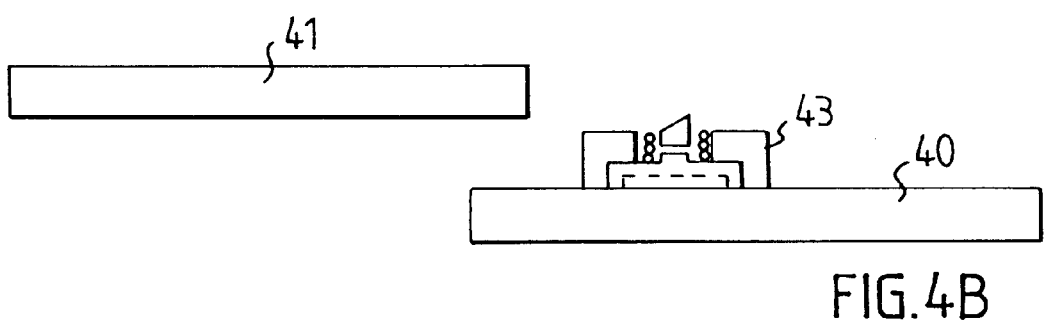
Figure 4C:
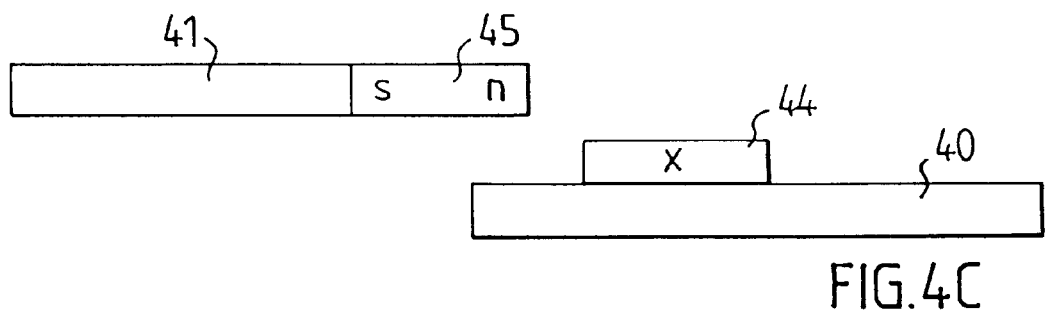
Figure 4D:
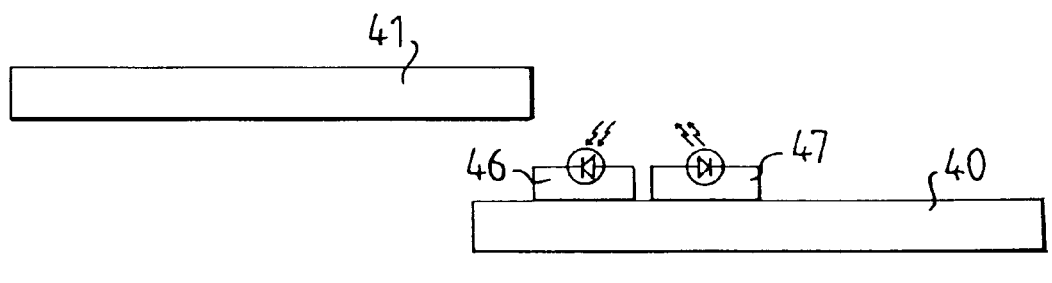

FIGS. 4A to 4D schematically illustrate alternative switch elements for use in a sensor. In all the Figures the main part of the switch element is mounted on a support 40 fixed in relation to a delivery device housing, whereas a part 41 is movable relative the support 40, although the opposite is also conceivable. Movable part 41 may be a needle cover or any other sensing part described. Movable part 41 is assumed to be displaceable from left to right in the drawings. In FIG. 4A switch element 42 houses a bistable contact plate flipping from one state to the other when pressed downwards by movable part 41. In FIG. 4B switch element 43 similarly becomes conductive when a resilient conductive mat is pressed over a gap in a conductive pattern on support 40. In FIG. 4C switch element 44 comprises a part sensitive to a magnetic field, such as a Hall element or a tongue element, and the movable part 41 comprises a magnetic element able to bring about a change of state in the switch 44. In FIG. 4D the switch comprises a radiation, e.g. IR, transmitter 46 and a radiation receiver 47 able to detect a change in received radiation caused by the presence and absence respectively of the movable part 41 over the receiver.

What is claimed is:

1. A delivery device including:
   a) a housing,
   b) a container for a fluid arranged in the housing, the container having an opening,
   c) a delivery conduit connected in fluid communication with the opening, the conduit having a front end in flow respect distal from the container and a rear end in flow respect proximal to the container, the front end and the rear end defining an axis therebetween and a forward direction and a rearward direction,
   d) a pump arranged to deliver fluid at least in a direction from the container through the conduit,
   e) a sensor able to change state in at least one respect in response to a predetermined proximity of an object to the sensor in a sensing direction,
   f) a converter, separate from or integral with the sensor, converting at least one of the sensor states into an electromagnetic signal, and
   g) a processor, receiving the electromagnetic signal and delivering a control signal to an operational component of the device.

2. The device of claim 1, wherein the container comprises an elongated barrel and a movable wall arranged therein and delimiting a chamber between the container opening and the movable wall.

3. The device of claim 2, wherein the chamber is divided into at least two chambers by at least one intermediate wall.

4. The device of claim 1, wherein the conduit front end is the termination of an injection channel.

5. The device of claim 1, wherein the conduit front end is designed for penetration into the object.

6. The device of claim 1, wherein the conduit front end is a needle or cannula.

7. The device of claim 1, wherein the pump comprises a cylinder and piston.

8. The device of claim 1, wherein the pump is electrically actuated.

9. The device of claim 1, wherein the sensor is able to change state at a distance from the object.

10. The device of claim 9, wherein the sensor includes a capacitive or inductive sensing element.

11. The device of claim 1, wherein the sensor is able to change state when in contact with the object.

12. The device of claim 11, wherein the sensor includes a pressure sensing element.

13. The device of claim 11, wherein the sensor includes a displacement sensing element.

14. The device of claim 11, wherein the sensor includes a switch element.

15. The device of claim 1, wherein the processor is a signal transmission line between the sensor and the operational component.

16. The device of claim 1, wherein the processor comprises signal processing circuitry arranged to process a signal versus time function.

17. The device of claim 16, wherein the processing performs one of a signal analogue to physical dampening, a calibration, an analogue to provision of physical hysteresis or a combination thereof.

18. The device of claim 1, wherein the device comprises a manual key and the processor is arranged to deliver the control signal only if the device is or has been activated.

19. The device of claim 1, wherein the operational component includes a message device able to issue a message to the user.

20. The device of claim 19, wherein the message device is able to deliver one of a tactically sensible signal, a visual signal, a display message or a combination thereof.

21. The device of claim 1, wherein the operational component includes an electromechanical device and the control signal is connected to enable or disable the electromechanical device.

22. The device of claim 21, wherein the electromechanical device includes one of a relay, solenoid, electric motor or a combination thereof.

23. The device of claim 21, wherein the electromechanical device is arranged to actuate or release at least the pump.

24. The device of claim 21, wherein at least the conduit front end is arranged movable in relation to the housing and the electromechanical device is arranged to actuate or release the movement.

25. The device of claim 24, wherein the movement actuated or released is in the forward and/or rearward direction.

26. The device of claim 1, wherein the sensing direction has at least one component parallel with the forward direction.

27. The device of claim 26, wherein the sensing direction is substantially parallel with the forward direction.

28. The device of claim 26, wherein the sensor is positioned with the predetermined proximity in given relationship to the conduit front end.

29. The device of claim 28, wherein the given relationship is with the predetermined proximity at, or forward of, the conduit front end, whereby sensor change of state takes place without conduit front end penetration into the object.

30. The device of claim 28, wherein the given relationship is with the predetermined proximity rearward of the conduit front end, when in its foremost position, whereby sensor change of state takes place with conduit front end penetration into the object.

31. The device of claim 30, wherein the given relationship is with the predetermined proximity at, or forward of, the conduit front end, when in its rearmost position, whereby conduit front end penetration into the object may take place with the sensor in the predetermined proximity to the object.

32. The device of claim 28, wherein the sensor comprises a movable part extending at least a distance between the conduit front end and the predetermined proximity position and sensor change of state takes place at a rearwardly displaced position for the movable part.

33. The device of claim 1, further comprising an object capable of being moved relative to the container, wherein the sensor is able to change state in at least one respect in response to a predetermined proximity of the object to the sensor in the sensing direction.

34. The device of claim 33, wherein the object is provided on a needle cover such that when the needle cover is moved to a predetermined position relative to the container, the sensor is able to change state.

35. A delivery device including:
a) a housing,
b) a container for a fluid arranged in the housing, the container having an opening,
c) a delivery conduit connected in fluid communication with the opening, the conduit having a front end in flow respect distal from the container and a rear end in flow respect proximal to the container, the front end and the rear end defining an axis therebetween and a forward direction and a rearward direction,
d) a pump arranged to deliver fluid at least in a direction from the container through the conduit,
e) a needle arranged at the conduit front end,
f) a needle cover arranged over at least an axial extension of the needle and being displaceable along a path substantially axial in relation to the needle,
g) a sensor able to change state in at least one respect in response to the presence of the needle cover in a predetermined position along said path, and
h) a converter, separate from or integral with the sensor, converting at least one of the sensor states into an electromagnetic signal.

36. A delivery device including:
a) a housing,
b) a container for a fluid arranged in the housing, the container having an opening,
c) a delivery conduit connected in fluid communication with the opening, the conduit having a front end in flow respect distal from the container and a rear end in flow respect proximal to the container, the front end and the rear end defining an axis therebetween and a forward direction and a rearward direction,
d) a pump arranged to deliver fluid at least in a direction from the container through the conduit,
e) a sensor able to change state in at least one respect in response to a predetermined proximity of an object to the sensor in a sensing direction having at least one component parallel with the forward direction, wherein the sensor is positioned with the predetermined proximity in given relationship to the conduit front end and comprises a movable part extending at least a distance between the conduit front end and the predetermined proximity position, wherein sensor change of state takes place at a rearwardly displaced position for the movable part, and wherein the movable part comprises a cover over at least a part of the conduit,
f) a converter, separate from or integral with the sensor, converting at least one of the sensor states into an electromagnetic signal, and
g) a processor, receiving the electromagnetic signal and delivering a control signal to an operational component of the device.

* * * * *